United States Patent [19]
Stevens et al.

[11] Patent Number: 5,618,928
[45] Date of Patent: Apr. 8, 1997

[54] TRIAZENYL-SUBSTITUTED PHENYL PYRIMIDINES AND THEIR USE IN THERAPY

[75] Inventors: Malcolm F. G. Stevens, Moseley; Daniel L. Rathbone, Earlsdon; Dennis M. O'Shea, Welwyn Garden City, all of England

[73] Assignee: British Technology Group Limited, London, England

[21] Appl. No.: 374,508

[22] PCT Filed: Jul. 1, 1993

[86] PCT No.: PCT/GB93/01381

§ 371 Date: Jan. 13, 1995

§ 102(e) Date: Jan. 13, 1995

[87] PCT Pub. No.: WO94/02469

PCT Pub. Date: Feb. 3, 1994

[30]   Foreign Application Priority Data

Jul. 15, 1992 [GB] United Kingdom .................. 9214994

[51] Int. Cl.⁶ .......................... C07C 245/24; A01N 33/26
[52] U.S. Cl. .......................... 534/551; 424/408; 424/464; 534/560; 534/565; 534/555; 534/775
[58] Field of Search .............................. 534/551; 514/150

[56]      References Cited

U.S. PATENT DOCUMENTS 3,162,571  12/1964  Adams et al. ....................... 534/551 X
4,092,305   5/1978  Townsend et al. ...................... 534/551

FOREIGN PATENT DOCUMENTS 0858814  1/1961  United Kingdom .................. 534/551
2268741  1/1994  United Kingdom .................. 534/551
WO84/04746  12/1984  WIPO ..................................... 534/551

OTHER PUBLICATIONS

Bliss et al, J. Chem. Soc. Perkins Trans. I, 1987, pp. 2217–2228.

Shusterman et al, Molecular Pharmacology, vol. 36 (6), pp. 939–944 (1989).

*Primary Examiner*—Floyd D. Higel
*Attorney, Agent, or Firm*—Nixon & Vanderhye

[57]            ABSTRACT

Compounds of formula I:

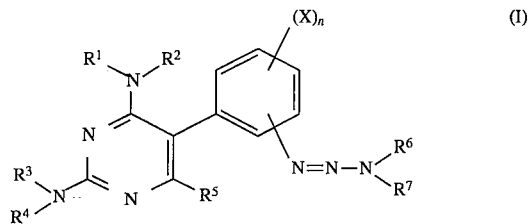

wherein $R^1$, $R^2$, $R^3$ and $R^4$ are each independently hydrogen, alkyl or acyl, $R^5$ is alkyl, X represents a hydrophobic substituent and n is an integer from 1 to 3, and $R^6$ and $R^7$ each represent alkyl, cycloalkyl, or aralkyl, or $R^6$ and $R^7$ together with the nitrogen to which they are attached form a heterocyclic ring, with the proviso that one or both of $R^6$ and $R^7$, or the heterocyclic ring including $R^6$ and $R^7$, carries and/or includes at least one oxygen or sulphur atom, or a salt or N-oxide thereof may be used in the treatment of *P. carinii* infections.

14 Claims, No Drawings

TRIAZENYL-SUBSTITUTED PHENYL PYRIMIDINES AND THEIR USE IN THERAPY

This invention relates to pyrimidine compounds and is particularly concerned with a class of triazenyl-substituted phenyl pyrimidine, for use in the chemotherapy of certain diseases commonly associated with AIDS or immuno-suppressed conditions resulting, for example, from cancer or organ transplantation.

The use of phenyl pyrimidines and purines in the therapy of diseases such as *Pneumocystis carinii* pneumonia, which is commonly associated with AIDS patients is known. The relative potency and selectivity of such compounds is discussed by Broughton and Queener, Antimicrobial Agents and Chemotherapy, July 1991, pages 1348–1355. The pyrimidine trimethoprim and the quinazoline trimetrexate are understood to target the enzyme dihydrofolate reductase (DHFR). Although of high potency, both such compounds have disadvantages in use. Thus trimethoprim used in combination with sulphamethoxazole is associated with a high percentage of adverse reactions in AIDS patients while the more potent trimetrexate has poor selectivity. These problems limit the usefulness of these agents, and they are reserved for use when the disease is so severe that the importance of side effects is diminished. Broughton and Queener also report experiments using pyrimethamine derivatives bearing a wide range of substituents at the meta and/or para position of the phenyl ring. However, the potencies obtained are many times less than those obtained with trimethoprim and trimetrexate while the selectivities obtainable are not sufficient to suggest that such compounds could displace the known drugs for treatment of *P. carinii* infections and other infections such as Toxoplasma associated with AIDS.

There is thus the need for development of new compounds capable of combatting such infections with sufficient selectivity to enable their use for a wide range of patients.

According to the present invention, there is provided a compound of formula I:

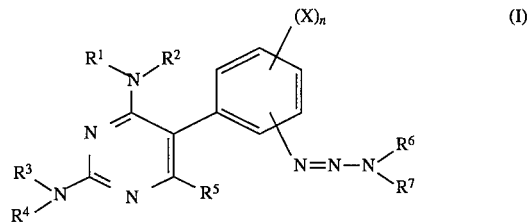

wherein $R^1$, $R^2$, $R^3$ and $R^4$ are each independently hydrogen, alkyl or acyl, $R^5$ is alkyl, X represents a hydrophobic substituent, for example halogen or alkoxy, and n is an integer from 1 to 3, and $R^6$ and $R^7$ each represent alkyl, cycloalkyl, or aralkyl, or $R^6$ and $R^7$ together with the nitrogen to which they are attached form a heterocyclic ring, with the proviso that one or both of $R^6$, and $R^7$, or the heterocyclic ring including $R^6$ and $R^7$, carries and/or includes at least one oxygen or sulphur atom, or a salt or N-oxide thereof.

Preferably $R^1$, $R^2$, $R^3$ and $R^4$ are hydrogen, although the invention also includes mono- and di-alkylated or acylated derivatives. $R^5$ is preferably lower alkyl e.g. containing up to 6 carbon atoms or more preferably ethyl.

X is preferably a halogen substituent, preferably chlorine, while n is usually 1. The hydrophobic substituent is preferably positioned meta or para to the pyrimidine ring, more preferably at the para position. Likewise, the triazene substituent is preferably meta or para to the pyrimidine ring and more preferably meta substituted.

A preferred group of compounds of formula I are those in which $R^6$ and $R^7$ each independently represent alkyl, or aralkyl, at least one of $R^6$ or $R^7$ carrying an oxygen-containing substituent, preferably a hydroxyl group, or including at least one oxygen atom, for example an alkoxyalkyl group or acyloxyalkyl group. Especially preferred are compounds where both of $R^6$ and $R^7$ represent a hydroxyethyl group or where one of $R^6$ and $R^7$ represents a hydroxyethyl group and the other represents a benzyl group or substituted benzyl group.

Also preferred are compounds where one of $R^6$ and $R^7$ represents an acyloxyalkyl group and the other represents a benzyl group or a substituted benzyl group.

A further preferred group of compounds of formula I are those in which $R^6$ and $R^7$ together with the nitrogen to which they are attached, form a morpholino group.

A preferred group of compounds in accordance with the invention are represented by formula II:

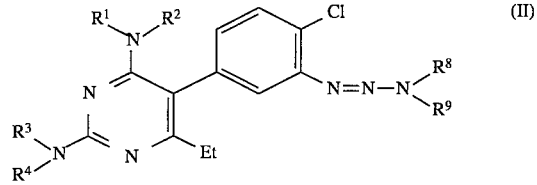

wherein $R^1$, $R^2$, $R^3$ and $R^4$ are as defined above, $R^8$ is alkyl or aralkyl and $R^9$ is hydroxyethyl, methoxyethyl or acetoxyethyl, or $R^8$ and $R^9$ together with the nitrogen to which they are attached form a morpholino group, or salts or N-oxides thereof.

Compounds of formula I and II above may conveniently be prepared according to the procedure described by Bliss et al., J. Chem. Soc. Perkin Trans., I, 1987, 2217–2228 and Griffin et al., J. Chem. Soc. Perkin Trans., I, 1985, 2267–2276, in accordance with the following general reaction scheme where $R^5$, X and n are as defined above:

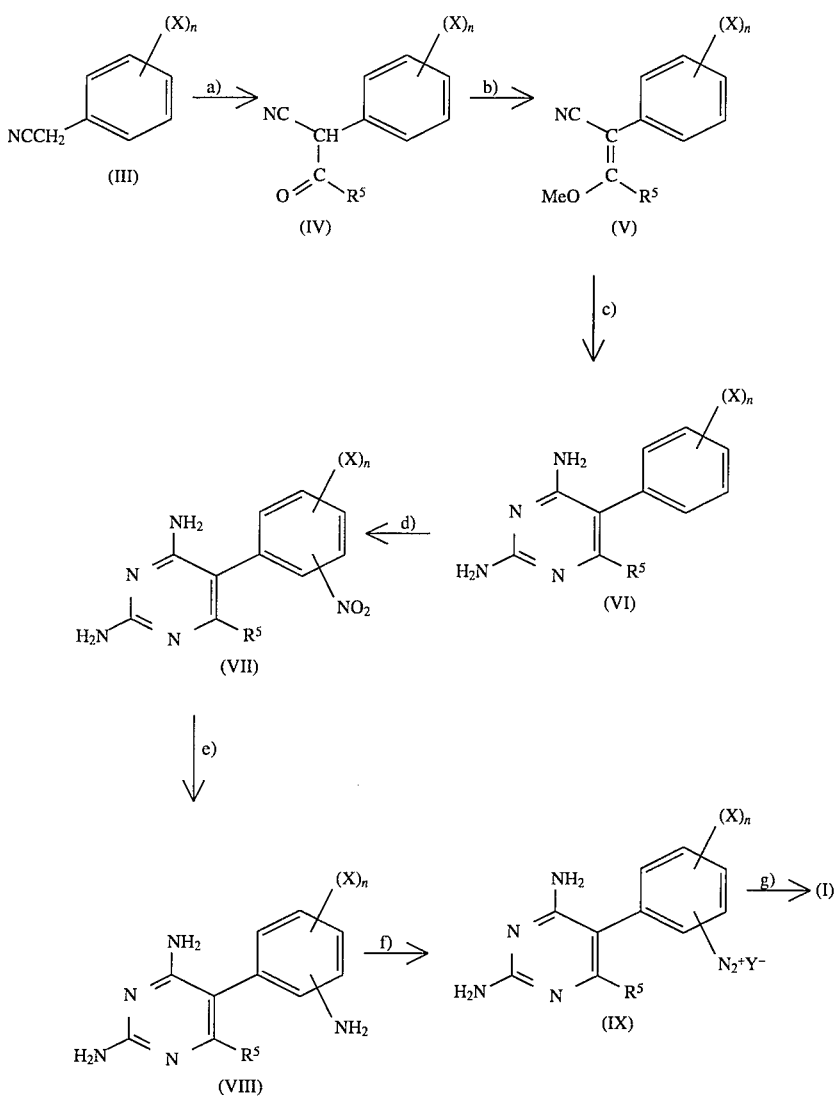

In accordance with the above scheme, an appropriately substituted phenylacetonitrile (III) is converted in step a) to the corresponding β-Keto nitrile (IV), for example by employing ethyl acetate or ethyl propionate in sodium ethoxide solution, and then in step b) to the corresponding methoxyacrylonitrile (V), for example using ethereal diazomethane. In step c), compound (V) is cyclised to yield diaminopyrimidine (VI), for example by cyclisation with guanidine in sodium ethoxide for 10 to 15 hours. Pyrimidine (VI) is then nitrated in step d) to the nitrophenyl-substituted pyrimidine (VII), for example by nitration with a mixture of concentrated nitric and sulphuric acids at 25° C., followed by reduction step e) in which the nitro derivative (VII) is converted to amino derivative (VIII), for example by the use of hydrazine-Raney nickel or tin (II) chloride in ethanol.

The amino derivatives (VIII) may be diazotised in step f), for example employing aqueous tetrafluoroboric acid to yield the diazonium tetrafluoroborate salt (IX) where $Y^-$ is $BF_4^-$. Salt (IX) can then be coupled with an appropriate amine of formula $HNR^6R^7$ where $R^6$ and $R^7$ are as defined above, followed by further optional derivatisation of the pyrimidine amino substituents or salt or oxide formation to yield compounds of formula (I) or salts or N-oxides thereof.

Alternatively, at least the compound pyrimethamine (VI where X is p-chloro and $R^5$ is ethyl) is commercially available as a starting material for steps d) to g).

Compounds of formula (I) as defined above have been shown to have considerable potency as inhibitors of *P. carinli* dihydrofolate reductase but reduced potency as inhibitors of rat liver dihydrofolate reductase, thus indicating usefulness in the treatment of infections of the type represented by *P. carinii* pneumonia.

This efficacy is surprising in view of the fact that dihydrofolate reductase inhibition is believed to occur as a result of interaction of the enzyme with a lipophtlic site on the inhibitor, so that introduction of addtional electron rich heteroatoms in a polar substituent is not a modification one would expect to make to improve inhibition.

Thus the invention further includes pharmaceutical compositions comprising as an active ingredient a compound of formula I or II as defined above or a pharmaceutically acceptable salt or N-oxide thereof. Furthermore, the invention includes the use of a compound of formula I or II as defined above, or a pharmaceutically acceptable salt or N-oxide thereof, in the treatment of parasitic infections associated with AIDS such as Pneumocystis and Toxoplasma, e.g. *P. carinii* infection.

The compositions may be administered by any suitable means, but preferably orally or possibly by intravenous injection. The administration will generally be carried out at intervals, for example one or several times per day.

The amount of compounds of formula (I), as herein defined which is required in order to be effective as an antibacterial agent for treating patients will, of course, vary and is ultimately at the discretion of the medical practitioner treating the patient in each particular case. The factors to be considered by such a practitioner, e.g. a physician, include the route of administration and pharmaceutical formulation; the patient's body weight, surface area, age and general condition; and the particular compound to be administered. However, a suitable effective dose is in the range of about 1 to about 10 mg/kg body weight, preferably in the range of about 1 to 5 mg/kg with most suitable doses being for example in the range 2 to 3 mg/kg. In daily treatment for example, the total daily dose may be given as a single dose, multiple doses, e.g. two to six times per day, or by intravenous infusion for any selected duration. For example for a 75kg patient, the dose range would be about 75 to 750 mg per day, and a typical dose would commonly be about 500 mg per day. If discrete multiple doses are indicated, treatment might typically be 125 mg of a compound of formula (I), as hereinbefore defined, given 4 times per day in the form of a tablet, capsule, liquid (e.g. syrup) or injection.

The nature of the acid participating in the acid addition salts may be of minor importance. However, when used medicine, the salts of these compounds of formula (I) will normally be pharmacologically and pharmaceutically acceptable, but non-pharmaceutically and non- pharmacologically acceptable salts may conveniently be used to prepare the free active compound or pharmaceutically acceptable salts thereof and are not excluded from the scope of this invention.

Suitable salts are those derived from, for example, the following acids: hydrochloric, hydrobromic, sulphuric, nitric, isethionic, phosphoric, maleic, salicylic, p-toluenesulphonic, tartaric, citric, lactobionic, formic, malonic, pantothenic, succinic, naphthalene-2-sulphonic, benzenesulphonic, methanesulphonic and ethanesulphonic. The preferred salts in terms of pharmaceutical acceptability are the ethanesulphonic acid salts.

While it is possible for the active compound of this invention to be administered alone as the raw chemical, it is preferable to present the active compound as a pharmaceutical formulation. Formulations of the present invention, for medical use, comprise the active compound together with one or more pharmaceutically acceptable carriers thereof and, optionally, any other therapeutic ingredients. The carrier(s) must be pharmaceutically acceptable in the sense of being compatible with the other ingredients of the formulation and not deleterious to the recipient thereof.

The formulations include those suitable for oral, rectal or parenteral (including subcutaneous, intramuscular and intravenous) administration.

The formulations may conveniently be presented in unit dosage form and may be prepared by any of the methods well known in the art of pharmacy. All methods include generally the step of bringing the active compound into association with a carrier which constitutes one or more accessory ingredients. Usually, the formulations are prepared by uniformly and intimately bringing the active compound into association with a liquid carrier or with a finely divided solid carrier or with both and then, if necessary, shaping the product into desired formulations.

Formulations of the present invention suitable for oral administration may be presented as discrete units such as capsules, cachets, tablets or lozenges, each containing a predetermined amount of the active compound; as a powder or granules; or a suspension in an aqueous liquid or non-aqueous liquid such as a syrup, an elixir, an emulsion or a draught. The active compound may also be presented as a bolus, electuary or paste.

A tablet may be made by compression or moulding, optionally with one or more accessory ingredients. Compressed tablets may be prepared by compressing, in a suitable machine, the active compound in a free-flowing form such as a powder or granules, optionally mixed with a binder, lubricant, inert diluent, surface active or dispersing agent. Moulded tablets may be made by moulding, in a suitable machine, a mixture of the powdered active compound with any suitable carrier.

A syrup may be made by adding the active compound to a concentrated, aqueous solution of a sugar, for example sucrose, to which may be added any accessory ingredient. Such accessory ingredient(s) may include flavourings, an agent to retard crystallisation of the sugar or an agent to increase the solubility of any other ingredient, such as a polyhydric alcohol for example glycerol or sorbitol.

Formulations suitable for parental administration conveniently comprise a sterile aqueous preparation of the active compound which is preferably isotonic with the blood of the recipient.

In addition to the aforementioned ingredients, formulations of this invention, for example ointments, creams and the like, may include one or more accessory ingredient(s) selected from diluents, buffers, flavouring agents, binders, surface active agents, thickeners, lubricants, preservatives (including antioxidants) and the like.

The invention with now be further described by way of example.

EXAMPLE 1

Preparation of intermediates from pyrimethamine a) 2,4,-Diamino-5-(4-chloro-3-nitrophenyl)-6-ethylpyrimidine 2,4,-Diamino-5-(4-chlorophenyl)-6-ethylpyrimidine (103.8 g, 0.417 mol) ("Pyrimethamine" obtained from Sigma Chemical Co. Ltd.) was added in portions to a stirred mixture of concentrated nitric acid (210 ml) and concentrated sulphuric acid (210 ml). The mixture was heated at 50° C. for 1 h and then set aside at room temperature for 2.5 days. The reaction mixture was poured onto concentrated ammonia ("0.88" 5 dm$^3$)/ice to effect a neutralisation. The resulting precipitate was collected by filtration and washed with water and sucked to dryness to give nitropyrimethamine as a yellow solid (115 g, 93.8% yield).

b) 2,4,Diamino-5-(3-amino-4-chorophenyl)-6-ethylprimidine

Method (i)

The nitrophenyipyrlmidine of a) above (40 g, 0.136 mol) was suspended in ethanol (500 ml). Raney nickel (40 g) was added and the mixture was stirred with heating from an oil bath set at 50°C. Hydrazine hydrate (400 ml) dissolved in ethanol (150 ml) was added dropwise over a 2 h period during which the reaction temperature did not exceed 60° C. The mixture was set aside at room temperature for 18 h, was filtered through Celite and was evaporated to dryness. The residue was recrystaillsed from ethanol to give aminopyrtmethamine (22.7 g, 0.086 mol, 63.3% yield).

Method (ii)

The nitrophenylpyrimidine of a) above (16.0 g) was added in small portions (over 15 min) to a stirred solution of tin (II) chloride dihydrate (38 g) in 10-hydrochloric acid (160 ml) at 5°–10° C. The mixture was stirred overnight and the white stannic complex collected. A solution of the stannic complex in hot water was basified to pH 12 with 10M-sodium hydroxide-ice. The white solid was collected and crystallised from ethanol to yield amber prisms of product title compound (9.5 g), mp 215°–217° C.

c) 2-Chloro-5-(2,4-diamino-6-ethylpyrimidin-5-yl)-benzenediazonium tetrafluoroborate hydrotetrafluroborate hemihydrate The amino phenyl pyrimidine of b) i) above (30 g, 0.114 mol) was suspended in 50% aqueous tetrafluoroboric acid (200 ml) and cooled to 0° C. A solution of sodium nitrite (8.63 g, 0.102 mol) in water (50 ml) was added dropwise. The mixture was stirred at 0° C. for 1 h and then was set aside in a freezer for 18 h. The ensuing precipitate was collected by filtration, was washed with a little cold water and then with diethyl ether. The solid was dried at room temperature under vacuum to give diazopyrimethamine tetrafluoroborate salt as a yellow powder (38 g). The exact number of tetrafluoroborate residues per diazopyrimethamine was not determined.

EXAMPLE 2

2,4-Diamino-5-(4-chloro-3-(3,3-bis-(2-hydroxyethyl)trizen-1-yl)phenyl)-6ethylpyrimidine
(Formula II: $R^1 \rightarrow R^4 = H$; $R^8 = R^9 = (CH_2)_2OH$)

The diazonium compound of Example 1(c) (3.0 g) was dissolved in water (60 ml) and cooled to 0° C. Diethanolamine (1.4 g, 13.3 mmol) dissolved in water (10 ml) was added and the mixture was stirred for 24 h. The solid product was collected by filtration and recrystallised from methanol to give the title compound (1.2 g) as a pale yellow powder, mp 218.7°–219.7° C., mw 379.5. The product was characterised by $^1$H-NMR spectroscopy and by microanalys.

$^1$H-NMR spectrum: ($d_6$-DMSO) δ ppm from TMS 0.98 (t, 3H, ArCH$_2$C$\underline{H}_3$); 2.12 (q, 2H, ArCH$_2$); 3.71 (m, 4H, NCH$_2$C$\underline{H}_2$OH); 3.88 (m, 4H, NC$\underline{H}_2$); 4.89 (bs, 2H, OH); 5.74 (bs, 2H, NH); 5.94 (bs, 2H, NH); 6.94 (dd, 1H, ArH); 7.19 (d, 1H, ArH); 7.49 (dd, 1H, ArH);

Microanalysis: Required (%) C 50.59; H 5.80; N 25.82
Found (%) C 50.36; H 5.78; N 25.32.

EXAMPLE 3

2,4,-Diamino-5-[4-chloro-3-(4-hydroxpiperdin-1-ylazo)phenyl]-6-etylpyrimidine

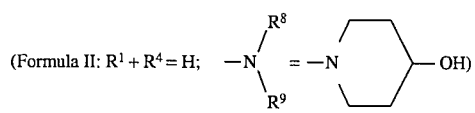

(Formula II: $R^1 + R^4 = H$;

Interaction of the diazonium compound of Example 1(c) (3.09 g) with 4-hydroxypiperidine (1.5 g) in water a 0° C. gave the title compound as a pale orange powder, mp 223.6°–224.9° C., mw 375.5. The product was characterised by $^1$H-NMR spectroscopy and by microanalysis.

$^1$H-NMR spectrum: ($d_6$-DMSO) δ ppm from TMS 0.98 (t, 3H, CH$_3$); 1.50 (m, 2H, ring CH$_2$); 1.82 (m, 2H, ring CH$_2$); 2.10 (q, 2H, Ar—C$\underline{H}_2$); 3.40, 3.60, 3.8, 4.10 (multipiers, 5H, ring CH$_2$/CH); 4.90 (m, 1H, OH); 5.65 (s, 2H, NH); 5.89 (s, 2H, NH); 6.91 (dd, 1H, Ar—H); 7.19 (d, 1H, ArH); 7.46 (d, 1H, Ar—H);

Microanalysis: Required (%) C 54.33; H 5.86; N 26.10
Found (%) C 52.84: H 6.33; N 24.03

EXAMPLE 4

2,4,-Diamino-5-[4-chloro-3-(4-morpholinylazo)phenyl]-6-ethylpyrimindine

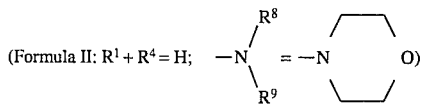

(Formula II: $R^1 + R^4 = H$;

A solution of the diazonium salt of Example 1(c) (2.5 g) was dissolved in water (70 ml) and cooled at 0° C. in an ice-bath. Morpholine (2.6 g) was added and the white precipitate of the title compound collected, dried and crystallised from ethanol. Yield 1.54 g, mp 247.2°–247.6° C., mp 361/363. The product was characterised by in,rated and $^1$H-NMR spectroscopy.

Infrared spectrum: (NuJol mull) 3440, 3380, 3320, 3140 (NH), 1628, 1562 cm$^{-1}$ $^1$H-NMR spectrum: ($d_6$-DMSO) δ ppm from TMS) 0.97 (t, 3H, ArCH$_2$C$\underline{H}_3$); 2.12 (q. 2H, ArCH$_2$); 3.80 (overlapping m, 8H, morpholine CH$_2$); 5.80 (s, 2H, NH) 5.98 (s, 2H, NH); 7.01 (dd, 1H, ArH); 7.24 (d, 1N, ArH); 7.51 (d, 1H, ArH)

EXAMPLE 5

2,4-Diamino-5-[4-chloro-3-(3-methyl-3-hydroxyethyltriazen-1-yl)phenyl]-6-ethyl-pyrimidine (Formula II: $R^1 \rightarrow R^4 = H$; $R^8 = CH_3$; $R^9 = (CH_2)_2OH$)

Interaction of the diazonium silt of Example 1(c) (3.0 g) and 2-hydroxyethylmethylamine (2.5 g) give the title compound as a pale yellow powder, mp 216.6°–217.1° C., mw 349.5. The product was characterised by $^1$H-NMR spectroscopy and microanalysis.

$^1$H-NMR spectrum: ($d_6$-DMSO) δ ppm from TMS 0.97 (t, 3H, ArCH$_2$C$\underline{H}_3$); 2.11 (q, 2H, Ar—C$\underline{H}_2$); 3.37 (s, 3H, NCH$_3$); 3.66 (d, 2H, C$\underline{H}_2$OH); 3.85 (m, 2H, NCH$_2$); 4.85 (bt, 1H, OH); 5.66 (s, 2H, NH); 6.92 (dd, 1H, ArH); 7.19 (d, 1H, ArH); 7.47 (d, 1H, ArH)

Microanalysis: Required (%) C 51.50; H 5.72; N 28.04
Found (%) C 51.66; H 5.74; N 28.01

EXAMPLE 6

2,4-Diamino-5-(4-chloro-3-(3-benzyl-3-(2-hydroxyethyl)triazen-1-yl)phenyl)-6-ethylpyrimidine
(Formula II: $R^1 \rightarrow R^4 = H$; $R^8 = CH_2Ph$; $R^9 = (CH_2)_2OH$)

The tetrafluoroborate salt of Example 1(a) (2.6 g) was dissolved in water (50 ml) and cooled to 0° C. N-Benzylethanolamine (8.1 g, 54 mmol) in water (10ml) was added and the mixture was stirred for 64 h. The solid product was collected by filtration and recrystalllsed from methanol to give the title compound (0.67 g) as a pale yellow powder, mp 112.1°–113.5° C., mw 425.5. The product was characterised by Infrared and $^1$H-NMR spectroscopy.

Infrared spectrum: (Nujol mull) 3438, 3395, 3297, 3159 (NH), 1625, 1555 cm$^{-1}$ $^1$H-NMR spectrum: (d$_6$-DMSO) δ ppm from TMS 0.98 (t, 3H, ArCH$_2$C$\underline{H}_3$); 2.12 (m, 2H, ArC$\underline{H}_2$CH$_3$); 3.71, 3.89, 4.10 (m, 4H, NC$\underline{H}_2$C$\underline{H}_2$); 4.91 (bs, 1H, OH); 5.05 (bs, 2H, PhC$\underline{H}_2$); 5.68 (bs, 2H, NH); 5.91 (bs, 2H, NH); 6.96 (m, 1H, ArH); 7.41 (overlapping m, 7H, ArH)

EXAMPLE 7

2,4-Diamino-5-(4-chloro-3-(3-ethyl-3-(2-hydroxyethyl)triazen-1-yl)phenyl)-6-ethylpyrimidine (Formula II: R$^1$→R$^4$=H; R$^8$=Et; R$^9$=(CH$_2$)$_2$OH)

Interaction of the diazonium salt of Example 1(c) (3.0 g) and 2-hydroxyethylethylamine (2.0 g) gave the title compound as an off-white powder, mp 214.3°–215.1° C., mw 363.5. The product was characterised by $^1$H-NMR spectroscopy and microanalysis.

$^1$H-NMR spectrum: (d$_6$-DMSO) δ ppm from TMS 0.97 (t, 3H, ArCH$_2$C$\underline{H}_3$); 1.23 (m, 2H, NCH$_2$C$\underline{H}_3$); 2.11 (q, 2H, ArCH$_2$); 3.8 (overlapping m, 6H, NC$\underline{H}_2$CH$_2$), NC$\underline{H}_2$CH$_3$); 4.86 (bs, 1H, OH); 5.64 (s, 2H, NH); 5.91 (s, 2H, NH); 6.92 (dd, 1H, Ar); 7.16 (d, 1H, ArH); 7.47 (d, 1H, ArH)

Microanalysis: Required (%) C 52.82; H 6.05; N 26.96
Found (%) C 53.02; H 6.05; N 26.84

EXAMPLE 8

2,4-Diamino-5-(4-chloro-3-(3-propyl-3-(2-hydroxyethyl)triazen-1-yl)phenyl)-6-ethylpyrimidine (Formula II: R$^1$→R$^4$=H; R$^8$=Pr; R$^9$=(CH$_2$)$_2$OH)

Interaction of the diazonium salt of Example 1(c) (3.0 g) and 2-hydroxyethylpropylamine (2.0 g) gave the title compound as an orange powder, mp 186.1–187.1; mw 377.5. The product was characterised by $^1$H-NMR spectroscopy and by microanalysis.

$^1$H-NMR spectrum: (d$_6$-DMSO) δ ppm from TMS 0.88 (m, 3H, NCH$_2$CH$_2$C$\underline{H}_3$); 0.98 (t, 3H, ArCH$_2$C$\underline{H}_3$); 1.70 (m, 2H, NCH$_2$C$\underline{H}_2$CH$_3$); 2.12 (q, 2H, ArC$\underline{H}_2$); 3.8 (overlapping m, 6H, NC$\underline{H}_2$CH$_2$CH$_3$), NC$\underline{H}_2$CH$_2$OH); 4.85 (s, 1H, OH); 5.70 (s, 2H, NH); 5.93 (s, 2H, NH); 6.93 (dd, 1H, ArH); 7.17 (d, 1H, ArH); 7.47 (d, 1H, ArH)

Microanalysis: Required (%) C 54.04; H 6.36; N 25.96
Found (%) C 54.30; H 6.31; N 26.16

EXAMPLE 9

2,4-Diamino-5-(4-chloro-3-(3t-butyl-3-(2-hydroxyethyl)triazen-1-yl)phenyl)-6-ethylpyrimidine (Formula II: R$^1$→R$^4$=H; R$^8$=t-Bu; R$^9$=(CH$_2$)$_2$OH)

Interaction of the diazonium salt of Example 1(c) (3.0 g) and 2-hydroxyethyl-t-butylamine (2.5 g) gave the title compound as fine beige crystals, mp 224.1°–225.4° C., mw 391.5. The product was characterised by $^1$H-NMR spectroscopy and by microanalysis.

$^1$H-NMR spectrum: (d$_6$-DMSO) δ ppm from TMS 0.98 (t, 3H, ArCH$_2$C$\underline{H}_3$); 1.41 (s, 9H, C(CH$_3$)$_3$); 2.10 (q, 2H, ArCH$_2$); 3.66 (m, 2H, NC$\underline{H}_2$CH$_2$); 3.81 (m, 2H, CH$_2$$_0$H); 4.78 (bs, 1H, OH); 5.60 (s, 2H, NH); 5.89 (s, 2H, NH); 6.91 (dd, 1H, ArH); 7.12 (d, 1H, ArH); 7.46 (d, 1H, ArH)

Microanaylsis: Required (%) C 55.17; H 6.64; N 25.03
Found (%) C 55.20; H 6.67; N 24.95

EXAMPLE 10

2,4Diamino-5-{4-chloro-3[3-benzyl-3-(2-acetoxyethyl)triazen-1-yl]phenyl}-6-ethylpyrimidine (Formula II: R$^1$→R$^4$=H; R$^8$=2-acetoxyethyl; R$^9$=benzyl)

2,4-diamino-5-(4-chloro-3-(3-benzyl-3-(2-hydroxyethy) triazen-1-yl)phenyl)-6-ethyl-pyrimidine(Example 6) (0.5 g) was added in portions over 30 minutes to make a solution of acetic anhydride (1.25 g), pyridine (0.4 g) and 4-dimethylaminopyridine (DMAP) (catalytic amount). The mixture was stirred overnight and water (25 ml) was added. After being stirred for 2 hours the precipitate was collected by filtration, washed with water and recrystallised from dimethylformamide followed by ethanol. The product (69%) had m.p. 166.2°–167.3°; (Found: C,58.77; H,5.66; N,20.5.

C$_{23}$H$_{26}$ClN$_7$O$_2$ requires: C,59.0; H,5.56: N,20.96%). The infrared spectrum (KBr disc) showed absorptions at 3451, 3192, 1723, 1628, 1553, 1445 and 1230 cm$^{-1}$.

The product was characterised by $^1$H-NMR spectroscopy.

$^1$H-NMR spectrum: (d$_6$-DMSO) δ ppm from TMS 0.96 (3H, t, C$\underline{H}_3$CH$_2$); 1.89 (3H, s, Me) 2.09 (2H, m, C$\underline{H}_2$CH$_3$); 3.92 (1H, bs, CH$_2$) 4.09 (1H, bs, CH$_2$); 4.27 (2H, s, CH$_2$) 5.02 (2H, s, PhCH$_2$); 5.63 (2H, s, NH) 5.89 (2H, s, NH); 6.97 (1 H, m, ArH) 7.35 (6H, m, ArH); 7.49 (1H, m, ArH)

It is also possible to make the compound (44%) by reacting the product of Example 6 (0.5 g) in pyridine (4.5 ml) containing DMAP (a few crystals), with acetyl chloride (0.1 g) at 25° C. for 18 hours. After shaking with water (75 mls) the solid was collected, washed with water and recrystallised as above.

EXAMPLE 11

2,4-Diamino-5-{4-chloro-3-[3,3-bis-(2-methoxyethyl)trizen-1-yl]phenyl}-6-ethyl pyrimidine (Formula II: R$^1$→R$^4$=H; R$^8$=R$^9$—(CH$_2$)$_2$OMe)

The method of Example 2 was repeated using the diazonium compound of Example 1(c) and di(2-methoxyethyl) amine to give the title compound as a peach coloured powder, mp 130.0°–132.0° C., mw 407.5, The product was characterised by $^1$H-NMR spectroscopy, $^1$H-NMR spectrum: (d$_6$-DMSO) δ ppm from TMS 0.96 (3H, t, C$\underline{H}_3$CH$_2$); 2.09 (2H, q, C$\underline{H}_2$CH$_3$) 3.26 (6H, d, CH$_3$O); 3.62 (4H, d, CH$_2$) 3.95 (4H, d, CH$_2$); 5.63 (2H, s, NH) 5.89 (2H, s, NH); 6.94 (1H, d, ArH) 7.16 (1H, d, ArH); 7.47 (1H, d, ArH)

EXAMPLE 12

Activity against *P. carinii* dihydrofolate reductase

The compounds described in Examples 2 to 9 were tested for inhibition of dihydrofolate reductase (DHFR) from *P. carinii* and from rat liver in accordance with the procedures described by Broughton and Queener, Antimicrobial Agents and Chemotherapy, 35, July 1991, 1348–1355.

The compounds were stored prior to use refrigerated in bags with desiccant. Stock solutions were made in neat DMSO and repeated freeze-thawing of stocks avoided. Testing was carried out against *P. carinii* and rat liver DHFR on the same day with fresh solutions.

Concentrations of drug producing 50% inhibition of control activity (IC50 values) were determined by probit analysis. Table 1 below gives the IC50 values for *P. carinii* DHFR ($P_c$) and rat liver DHFR (RL) and the ratio of these IC50 values as a measure of selectivity of the compounds.

TABLE 1

| Compound of Example | μM IC50 Pc | μM IC50 RL | IC50 RL/IC50 Pc |
|---|---|---|---|
| 2 | 0.44 | 5 | 11.4 |
| 3 | 3.3 | 7.2 | 2.2 |
| 4 | 1.7 | 26.3 | 15.3 |
| 5 | 3.5 | 27.9 | 8 |
| 6 | 0.26 | 7 | 26.7 |
| 7 | 11.5 | 27 | 2.3 |
| 8 | 2.5 | 0.44 | 0.2 |
| 9 | 4.9 | 10.3 | 2.1 |
| 10 | 0.17 | 19.4 | 114 |
| 11 | 0.91 | 26.1 | 29 |

EXAMPLE 13

Activity against *T. gondii* dihydrofolate reductase

The compounds described in Examples 4, 10 and 11 were tested for inhibition of dihydrofolate reductase from *T. gondii* and from rat liver using a procedure similar to that used for *P. carinii* (Example 12).

The *T. gondii* assay for the compound of Example 4 was performed with frozen drug stock and not run at the same time as the rat liver DHFR.

The results are given in Table 2 below as IC50 values for *T. gondii* DHFR (Tx) and rat liver DHFR (RL) and the ratio of these IC50 values as a measure of selectivity of the compounds.

TABLE

| Compound of Example | mM IC50 Tx | mM IC50 RL | IC50 RL/IC50 Tx |
|---|---|---|---|
| 4 | 0.19 | 26.3 | 138 |
| 10 | 0.69 | 19.4 | 28 |
| 11 | 8.8 | 26.1 | 3 |

We claim:
1. A compound of formula I:

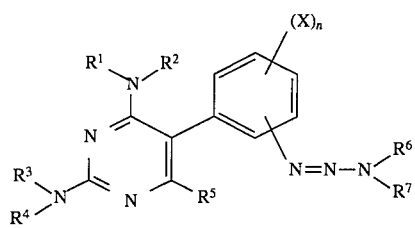

wherein $R^1$, $R^2$, $R^3$ and $R^4$ are each independently hydrogen or alkyl, $R^5$ is alkyl, X represents halogen or alkoxy, and n is an integer from 1 to 3, and $R^6$ and $R^7$ each represent alkyl, cycloalkyl, or aralkyl, wherein at least one of $R^6$ and $R^7$ is substituted by a hydroxyl, alkoxy or acyloxy group, or $R^6$ and $R^7$ together with the nitrogen to which they are attached from a heterocyclic ring selected from the group consisting of:

a heterocyclic ring including at least one oxygen or sulfur atom, and a heterocyclic ring not including an oxygen or sulfur atom but which optionally carries a hydroxyl group, or a salt or N-oxide thereof.

2. A compound according to claim 1, or a salt or N-oxide thereof, wherein $R^1$, $R^2$, $R^3$ and $R^4$ are hydrogen.

3. A compound according to claim 1, or a salt or N-oxide thereof, wherein $R^5$ is ethyl.

4. A compound according to claim 1, or a salt or N-oxide thereof, wherein X is chlorine.

5. A compound according to claim 1, or a salt or N-oxide thereof, wherein n is 1 and X is positioned meta or para to the pyrimidine ring.

6. A compound according to claim 1, or a salt or N-oxide thereof, wherein the triazene substituent is positioned meta or para to the pyrimidine ring.

7. A compound according to claim 1, or a salt or N-oxide thereof, wherein $R^6$ and $R^7$ each independently represent alkyl, or aralkyl, at least one of $R^6$ or $R^7$ being substituted with a hydroxyl, alkoxy or acyloxy group.

8. A compound according to claim 7, or a salt or N-oxide thereof, wherein each of $R^6$ and $R^7$ represents a hydroxyethyl group or wherein one of $R^6$ and $R^7$ represents a hydroxyethyl group and the other represents a benzyl group or substituted benzyl group.

9. A compound according to claim 7, or a salt or N-oxide thereof, wherein one of $R^6$ and $R^7$ represents an acyloxyalkyl group and the other represents a benzyl group or substituted benzyl group.

10. A compound according to claim 1, or a salt or N-oxide thereof, wherein $R^6$ and $R^7$ together with the nitrogen to which they are attached form a morpholino group.

11. A compound of formula II

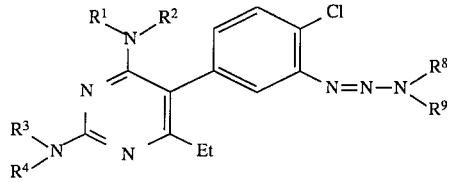

wherein $R^1$, $R^2$, $R^3$ and $R^4$ are as defined in claim 1, $R^8$ is alky or aralkyl, hydroxyethyl or methoxyethyl, and $R^9$ is hydroxyethyl, methoxyethyl or acetoxyethyl, or $R^8$ and $R^9$ together with the nitrogen to which they are attached from a morpholino group, or a salt or N-oxide thereof, or a 4-hydroxypiperidine group.

12. A pharmaceutical composition comprising as active ingredient a compound of formula I as defined in claim 1 or a pharmaceutically acceptable salt or N-oxide thereof.

13. A pharmaceutical composition comprising as active ingredient a compound of formula II as defined in claim 11 or a pharmaceutically acceptable salt or N-oxide thereof.

14. A method for treatment of a parasitic infection in a patient in need of such treatment, said method comprising administering an effective amount of a compound as defined in claim 1 or a pharmaceutically acceptable salt or N-oxide thereof to said patient.

* * * * *